United States Patent
Morningstar

(10) Patent No.: US 9,211,173 B2
(45) Date of Patent: *Dec. 15, 2015

(54) INCONTINENCE TREATMENT DEVICE

(71) Applicant: Coloplast A/S, Humlebaek (DK)

(72) Inventor: Randy L. Morningstar, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 78 days.

This patent is subject to a terminal disclaimer.

(21) Appl. No.: 14/084,634

(22) Filed: Nov. 20, 2013

(65) Prior Publication Data

US 2014/0073844 A1    Mar. 13, 2014

Related U.S. Application Data

(63) Continuation of application No. 12/792,735, filed on Jun. 3, 2010, now Pat. No. 8,617,050.

(30) Foreign Application Priority Data

Jun. 8, 2009  (DK) .................................. 2009 00718

(51) Int. Cl.
*A61F 2/00*  (2006.01)

(52) U.S. Cl.
CPC ............... *A61F 2/0013* (2013.01); *A61F 2/004* (2013.01); *A61F 2/0045* (2013.01); *A61F 2/0063* (2013.01)

(58) Field of Classification Search
CPC ..... A61F 2/004; A61F 2/0063; A61F 2/0013; A61F 2/0045
See application file for complete search history.

(56) References Cited

U.S. PATENT DOCUMENTS

| | | | |
|---|---|---|---|
| 3,863,622 A * | 2/1975 | Buuck | 600/31 |
| 4,890,866 A | 1/1990 | Arp | |
| 5,041,136 A * | 8/1991 | Wascher et al. | 623/23.65 |
| 5,348,210 A * | 9/1994 | Linzell | 228/115 |
| 5,562,598 A | 10/1996 | Whalen et al. | |
| 6,387,071 B1 | 5/2002 | Constantz | |
| 7,393,319 B2 | 7/2008 | Merade et al. | |
| 7,395,822 B1 * | 7/2008 | Burton et al. | 128/885 |
| 7,422,557 B2 | 9/2008 | Arnal et al. | |
| 7,431,690 B2 | 10/2008 | Merade et al. | |
| 7,611,454 B2 | 11/2009 | De Leval | |
| 7,621,864 B2 | 11/2009 | Suslian et al. | |
| 2002/0115906 A1 | 8/2002 | Miller | |
| 2003/0069619 A1 | 4/2003 | Fenn et al. | |
| 2004/0138523 A1 | 7/2004 | Kuyava et al. | |

(Continued)

FOREIGN PATENT DOCUMENTS

CN    1074285    7/1993

*Primary Examiner* — Christine H Matthews
*Assistant Examiner* — Joshua D Lannu
(74) *Attorney, Agent, or Firm* — Coloplast Corp., Coloplast A/S; Nick Baumann

(57) ABSTRACT

An incontinence treatment device includes a support, a pump, and anchors each attached to a connection line. The support includes an inflatable bladder and the pump is body-implantable and attachable to the inflatable bladder. The pump is configured to selectively inflate the inflatable bladder to compress the tissue of the urethra. The connection lines are attached to the support. A first anchor is fixed to the first connection line and a second anchor is coupled to the second connection line, where the second anchor is an adjustable anchor. The adjustable anchor is configured to be movable and position-adjustable relative to the second connection line.

15 Claims, 13 Drawing Sheets

(56) References Cited

U.S. PATENT DOCUMENTS

| | | |
|---|---|---|
| 2005/0055104 A1 | 3/2005 | Arnal et al. |
| 2005/0101834 A1 | 5/2005 | Merade |
| 2005/0283040 A1 | 12/2005 | Greenhalgh |
| 2006/0052800 A1 | 3/2006 | Greenhalgh |
| 2006/0122457 A1 | 6/2006 | Kovac et al. |
| 2007/0049791 A1 | 3/2007 | Merade et al. |
| 2010/0198003 A1* | 8/2010 | Morningstar et al. .......... 600/37 |

* cited by examiner

INCONTINENCE TREATMENT DEVICE

BACKGROUND

Implantable devices are available that provide support to anatomical organs of a patient to treat urinary incontinence. Such devices have included sub-urethral slings that provide tension to the male urethra, for example, in reducing the discomfort and inconvenience related to urinary incontinence. These sling devices are surgically implanted under a patient's urethra to provide support to the urethra so that urine is inhibited from leaking out of the urethra during a provocative event such as coughing or laughing.

Implanting and anatomically securing some sling devices may be difficult and time consuming. In addition, in the case of urinary incontinence, some sling devices may provide unreliable anatomical fixation and/or imperfect tensioning for supporting the urethra, thereby leading to suboptimal or even unacceptable results for the treatment of urinary incontinence.

SUMMARY

One aspect provides an anatomical augmentation device configured to augment a tubular member of a human body. The device includes an inflatable bladder, a support coupled to the inflatable bladder, and a pump coupleable with the inflatable bladder. The support includes a first connection line and a second connection line that are each attachable to soft tissue to position the inflatable bladder relative to the tubular member of the human body. The device is a body-implantable device and the pump is configured to selectively inflate the inflatable bladder to occlude the tubular member of the human body.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

An anatomical augmentation device is defined to mean a device that is selectively activated to support a portion of the anatomical structure. For example, one embodiment of an anatomical augmentation device supports a urethra by supporting spongy tissue that surrounds the urethra and is configured to be patient-activated to occlude the urethra by compressing the spongy tissue and the urethra. Another embodiment of an anatomical augmentation device supports the urethra by contacting the urethra and is configured to be patient-activated to occlude the urethra by compressing the urethra.

Soft tissue includes dermal tissue, sub-dermal tissue, ligaments, tendons, or membranes but does not include bone.

Embodiments provide an anatomical augmentation device configured to selectively occlude a tubular member of a human body (male or female) in a manner that reduces or eliminates erosion of the tubular member.

Embodiments provide an anatomical augmentation device configured to hydraulically occlude and thus impede liquid flow through a urethra (male or female), also in a manner that reduces or eliminates erosion of the urethra.

One embodiment provides an anatomical device that is attachable to obturator membrane in the form of an adjustable sling, where the sling includes an inflatable bladder positionable near the patient's urethra. The patient selectively inflates the bladder to coaptate (or close) the urethra to prevent leakage of urine. Subsequently, the patient selectively deflates the bladder to release the pressure on the urethra to open a pathway for the passage of urine.

One embodiment provides an anatomical device implantable into a patient that enables the patient to urinate freely after the patient activates a mechanical component of the anatomical device. In this manner, the patient is empowered to control urine retention and urine voiding.

Figure 1:
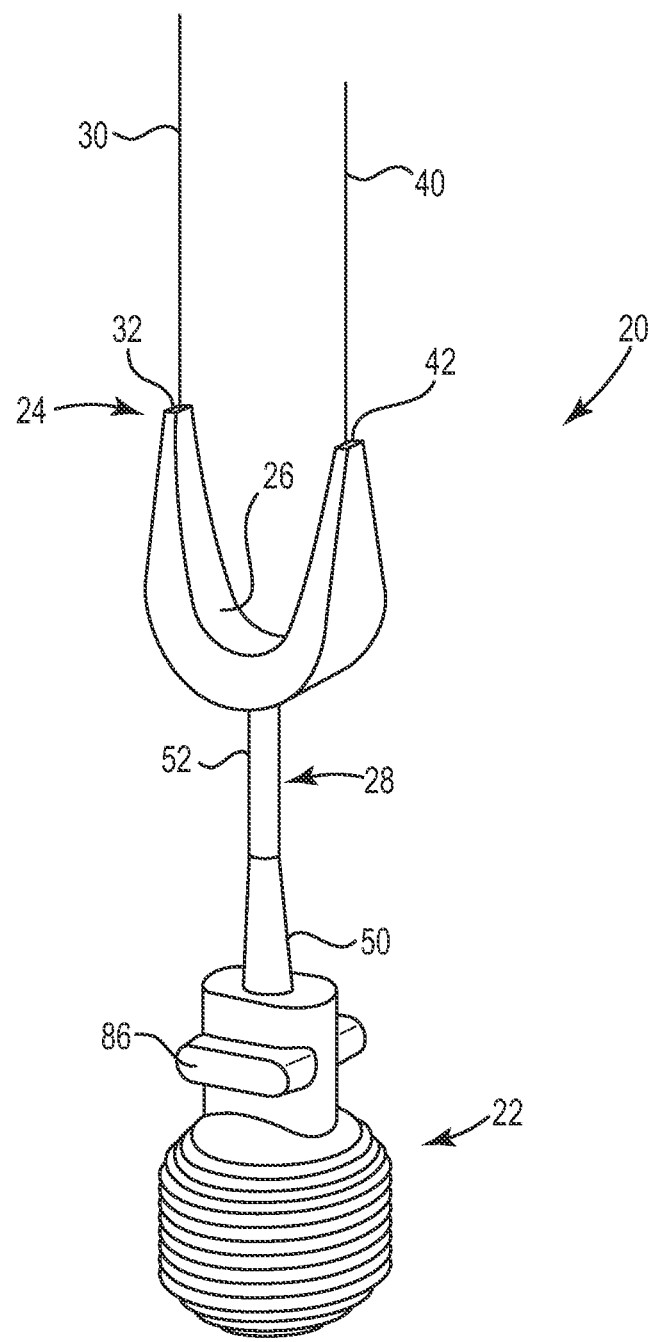
FIG. 1 is a front perspective view of an anatomical augmentation device including an inflatable bladder and a pump communicating with the inflatable bladder according to one embodiment.

FIG. 1 is a perspective view of an anatomical augmentation device 20 according to one embodiment. Anatomical augmentation device 20 (device 20) includes a pump 22, a support 24 coupled to an inflatable bladder 26, and a conduit 28 providing fluid communication between pump 22 and inflatable bladder 26. In one embodiment, support includes a first connection line 30 coupled to a first end 32 of inflatable bladder 26 and a second connection line 40 coupled to a second end 42 of inflatable bladder 26, where the first and second connection lines 30, 40 are each attachable to soft tissue in a patient to position inflatable bladder 26 relative to a tube (e.g., a tube or a duct) of the patient. Pump 22 couples with and is configured to selectively inflate inflatable bladder 26. In this manner, inflatable bladder 26 is anchored relative to the tube, and inflation of inflatable bladder 26 occludes the tube to impede liquid flow through the tube.

In one embodiment, pump 22 includes a pump conduit 50 that is removably attachable to an inflatable bladder conduit 52, for example via a connector. In one embodiment, pump conduit 50 is integrally formed as a single piece with bladder conduit 52.

Figure 10A:
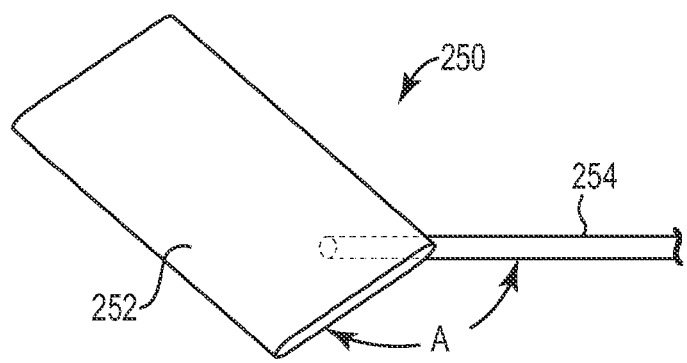
FIG. 10A is a perspective view of one embodiment of a deflated bladder and FIG. 10B is a perspective view of the bladder in an inflated state.
Figure 10B:
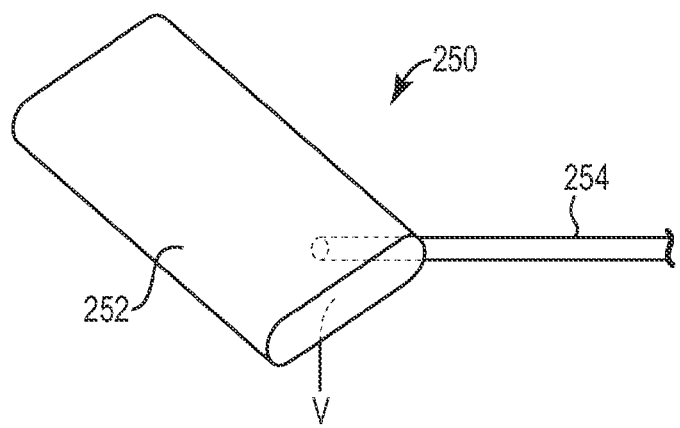

In one embodiment, support 24 and inflatable bladder 26 are integrally molded as a single unit. Inflatable bladder 26 may be fabricated in a rectilinear form (e.g., a flat rectangular pillow as illustrated in FIGS. 10A and 10B) or a curvilinear form (e.g., annular or half-annular form as illustrated in FIG. 1) or in other suitable forms. For example, in one embodiment inflatable bladder 26 is molded to provide a semi-annular inflatable bladder sized to be disposed around the bulbous spongiosum surrounding the urethra.

In one embodiment, inflatable bladder 26 is provided with a length between approximately 5-12 cm having a width between approximately 1-6 cm, although the size of bladder 26 is not critical.

Figure 2:
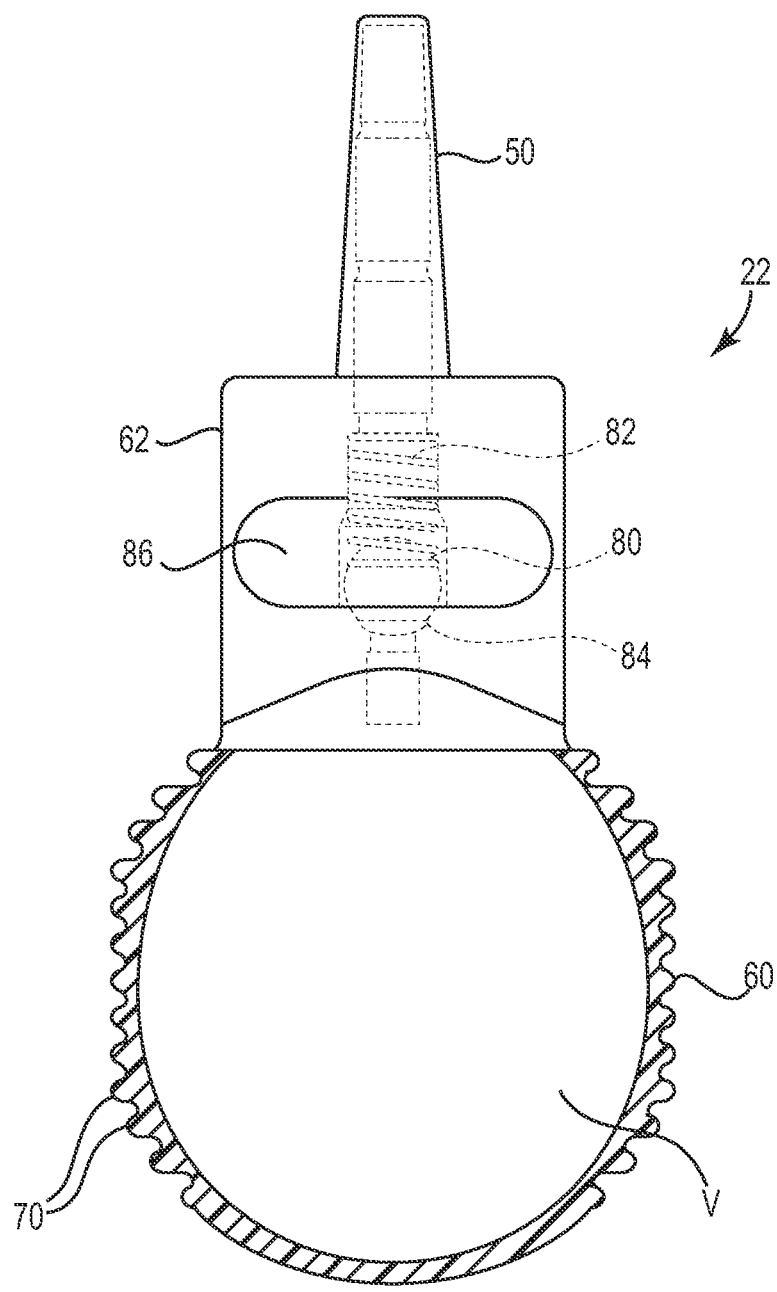
FIG. 2 is a schematic cross-sectional view of the pump illustrated in FIG. 1 according to one embodiment.

FIG. 2 is a schematic cross-sectional view of pump 22 according to one embodiment. Pump 22 includes a bulb 60 sized to retain a liquid volume V and a valve housing 62 extending between bulb 60 and pump conduit 50. In one embodiment, bulb 60 is formed of silicone and includes an articulated housing 70 that is configured to be sufficiently resilient to enable a patient to expel a sufficient volume of liquid from bulb 60 to inflate inflatable bladder 26. In one embodiment, bulb 60 is sufficiently resilient to enable the patient to expel a sufficient volume of liquid from bulb 60 to inflate inflatable bladder 26 with one squeeze. Other styles and forms of squeezable bulbs are also acceptable. Suitable liquids to be retained in bulb 60 for activating inflatable bladder 26 (FIG. 1) include fluids in general, examples of which include water or a saline solution of water. Preferably the liquid is a sterile saline solution.

In one embodiment, valve housing 62 encloses a ball valve 80 or check valve 80, a biasing member 82, and a seat 84 sized to receive ball valve 80. In one embodiment, compressing bulb 60 ejects the liquid volume V into or toward pump conduit 50 with sufficient force to lift ball valve 80 off of seat 84. Biasing member 82 is subsequently compressed, which provides a fluid passageway between ball valve 80 and seat 84 that allows the liquid inside of bulb 60 to flow through pump conduit 50 and inflate inflatable bladder 26 (FIG. 1). When the pressure (e.g., squeeze) applied to bulb 60 is relieved, biasing member 82 biases ball valve 80 back into engagement with seat 84, which closes the fluid passageway between ball valve 80 and seat 84 to ensure that the liquid remains in inflatable bladder 26 and inflatable bladder 26 remains inflated. In this state, bulb 60 is "cavitated" to have a lower pressure than the pressure in inflatable bladder 26, which "primes" bulb 60 to eventually suction or pull the liquid from inflatable bladder 26 back into bulb 60 when ball valve 80 is displaced from seat 84, for example when the patient desires to deflate inflatable bladder 26.

In one embodiment, valve housing 62 includes a pressure relief feature 86 that is configured to deform seat 84 when pressure relief feature 86 is activated. Deformation of seat 84 interrupts the seal between ball valve 80 and seat 84 to enable the liquid in inflatable bladder 26 to flow through pump conduit 50 and back into bulb 60. For example, in one embodiment valve housing 62 is formed of silicone, and squeezing the silicone enclosure of pressure relief feature 86 deforms housing 62 and creates a space or an opening between ball valve 80 and seat 84, which allows the liquid in inflatable bladder 26 to flow through pump conduit 50 and back into bulb 60. Other forms of pressure relief features, including mechanical and/or electro-mechanical pressure relief features are also acceptable.

In one embodiment, and with reference to FIG. 1, conduit 28 between pump 22 and inflatable bladder 26 is provided in a fixed length such that pump conduit 50 and inflatable bladder conduit 52 are formed as a single integral conduit. However, it may be desirable (e.g., for differently sized patients) to provide a connector to couple pump conduit 50 to an inflatable bladder conduit 52 of a selected length to accommodate patients ranging in size from adolescent-sized to adult sized.

Figure 3A:
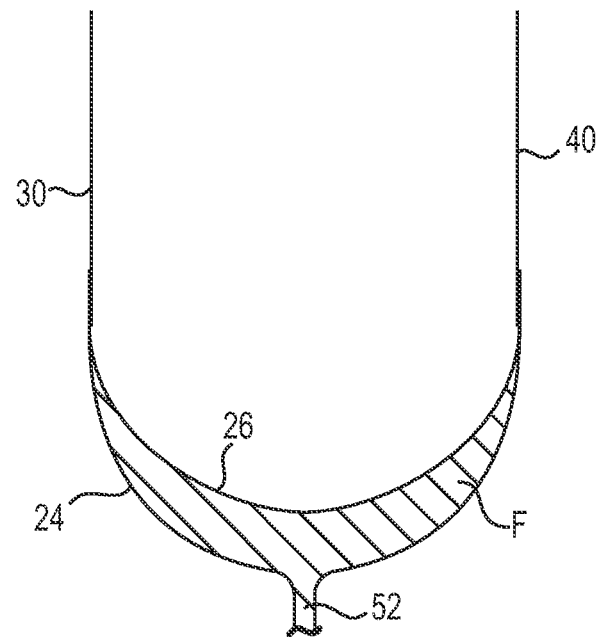
FIG. 3A is a side view of the inflatable bladder illustrated in FIG. 1 after inflation.
Figure 3B:
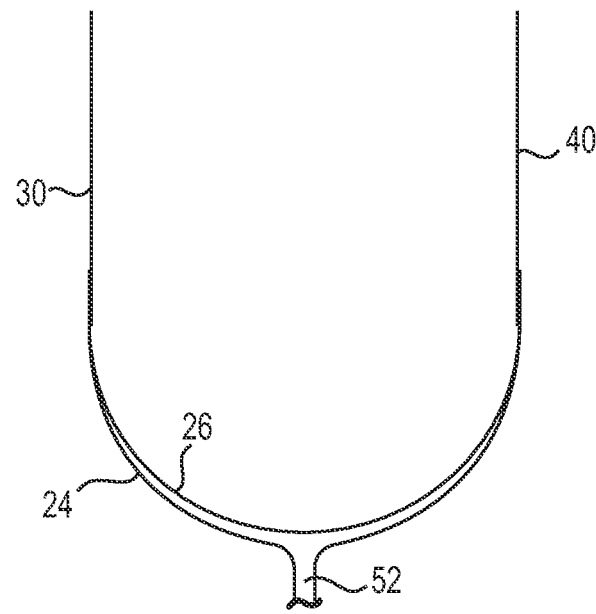
FIG. 3B is a side view of the inflatable bladder illustrated in FIG. 1 prior inflation or after deflation.

FIG. 3A is a side view of the inflatable bladder 26 after inflation and FIG. 3B is a side view of the inflatable bladder 26 prior to inflation or after deflation. In one embodiment, support 24 is a silicone surface or film that is sealed on its periphery to an inflatable bladder 26 surface and includes an opening communicating with bladder conduit 52. In one embodiment, support 24 and inflatable bladder 26 are integrally formed as a monolithic unit, for example via molding. Connection lines 30, 40 are attached to support 24, and in one embodiment are molded into connection with support 24 as support and inflatable bladder 26 are formed. Connection lines 30, 40 may also be suitably attached to support 24 by other means, such as sutures, adhesives, etc.

Connection lines 30, 40 are provided to allow a surgeon to place support 24 and inflatable bladder 26 in a region near a tube or a duct of the patient who would benefit from selective, patient-controlled opening/closing of the tube/duct. For example, and as described more fully below, in one embodiment connection lines 30, 40 are terminated in tissue of the patient (for example each line 30, 40 is attached to an obturator membrane covering the obturator foramen) to locate support 24 near the bulbous spongiosum surrounding the urethra (U in FIG. 9A) of the patient. In this manner, support 24 of anatomical augmentation device 20 (FIG. 1) is fixed in place relative to the urethra, and inflating inflatable bladder 26

(FIG. 3A) compresses and coaptates the urethra. For example, a patient may desire to close or coaptate the urethra (by squeezing bulb 60 in FIG. 2) during the daytime active period. Deflating inflatable bladder 26 as illustrated in FIG. 3B collapses bladder 26 toward support 24, which decompresses bladder 26 and enables the urethra to return to its open position. For example, a patient may open the urethra (by pressing relief feature 86 in FIG. 2) to void urine, or during the nighttime sleep period when the urge to void is reduced.

Figure 4:
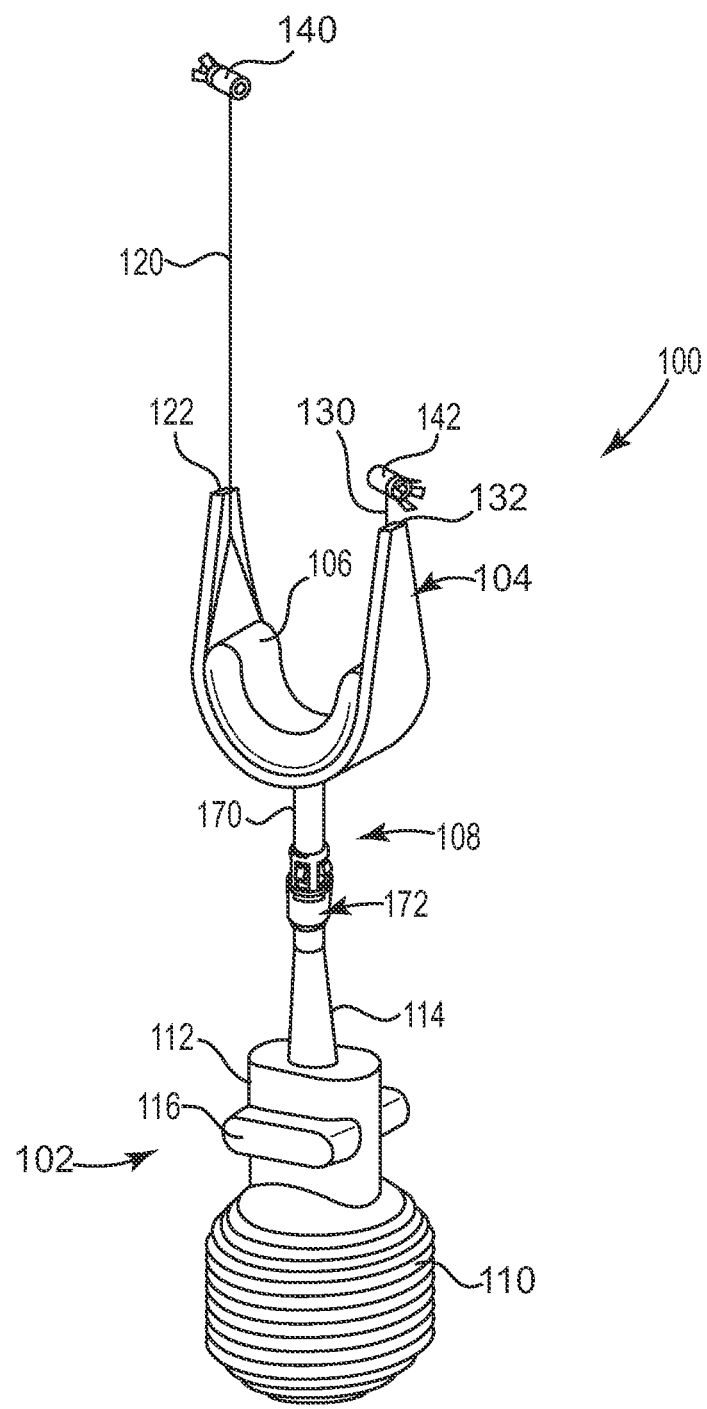
FIG. 4 is a perspective view of an anatomical augmentation device including an inflatable bladder attached to a mesh support that is provided with an adjustable anchor according to one embodiment.

FIG. 4 is a perspective view of an anatomical augmentation device 100 according to one embodiment. Anatomical augmentation device 100 (device 100) includes a pump 102, a support 104 coupled to an inflatable bladder 106, and a conduit 108 providing fluid communication between pump 102 and inflatable bladder 106.

In one embodiment, pump 102 is similar to pump 22 (FIG. 2) and includes a bulb 110 of volume V, a valve housing 112 extending between bulb 110 and a pump conduit 114, where valve housing 112 includes a pressure relief feature 116 similar to pressure relief feature 86 described above in FIG. 2.

In one embodiment, support 104 is a mesh configured to be compatible with and enable tissue in-growth to the mesh to additionally support/retain device 100 after implantation. One suitable mesh is a knitted polypropylene mesh. Other suitable meshes are also acceptable for use as support 104. In one embodiment, support 104 is substantially the same size as inflatable bladder 106. In one embodiment, support 104 is substantially different in size as compared to inflatable bladder 106

In one embodiment, support 104 includes a first connection line 120 coupled to a first end 122 of support 104, a second connection line 130 is coupled to a second end 132 of support 104, a first anchor 140 attached to first connection line 120, and a second anchor 142 attached to second connection line 130. In one embodiment, connection lines 120, 130 are surgical sutures, or twined portions of the knitted polypropylene mesh material, although other forms of lines suited for implantation into the human body are also acceptable.

In one embodiment, at least one of the anchors 140, 142 (for example anchor 140) is an adjustable anchor that is configured to slide along a respective one of the connection lines 120, 130 to enable selective positioning and tensioning of support 104 and bladder 106 anatomically within a patient. For example, adjustable anchor 140 slides along connection line 120 to enable elevating the urethra. In particular, when employing device 100 to augment female anatomy, adjustable anchor 140 slides along connection line 120 to desirably elevate the urethra without compressing the urethra. In other words, adjustable anchor 140 enables elevating the urethra with approximately zero tension applied to the urethra. In addition, adjustable anchor 140 in one embodiment is configured to slide along connection line 120 to both elevate and apply tension to the urethra. In particular, when employing device 100 to augment male anatomy, adjustable anchor 140 slides along connection line 120 to desirably elevate and apply tension to the urethra.

In one embodiment, a length of line 120 is between 2-20 cm, approximately, and a length of connection line 130 is between 0.5-2 cm, approximately. The length of line 130 is selected such that when anchor 142 is secured to soft tissue, an approximate mid-point of inflatable bladder is disposed adjacent the patient's urethra. Adjustable anchor 140 enables the selective adjustment of the length of line 120 between end 122 of support 104 and anchor 140 to enable the surgeon to position and tension support 104 and bladder 106 to desired levels.

Figure 5A:
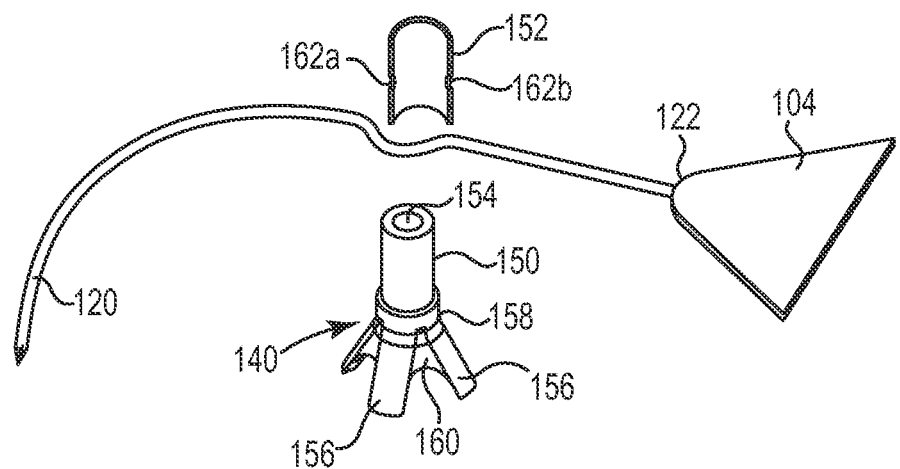
FIG. 5A is an exploded perspective view and FIG. 5B is a top view of the adjustable anchor illustrated in FIG. 4 relative to a connection line according to one embodiment.
Figure 5B:
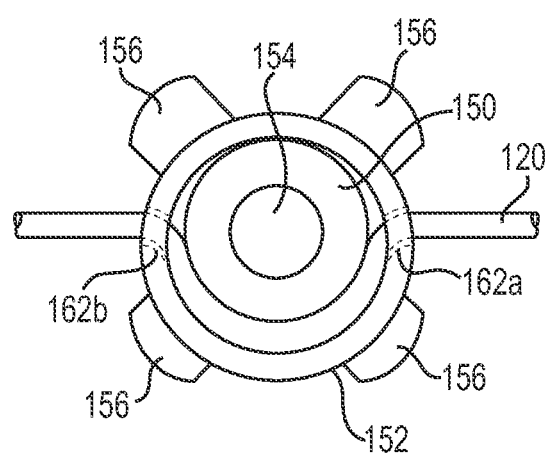

FIG. 5A is an exploded perspective view and FIG. 5B is a top view of adjustable anchor 140 and connection line 120 illustrated in FIG. 4 according to one embodiment. Adjustable anchor 140 includes a body 150 and a collar 152 sized to frictionally capture connection line 120 against body 150. Other forms of adjustable anchor 140 configured to frictionally capture and engage with connection line 120 are also acceptable. Various such adjustable anchors are disclosed in, for example, co-pending and commonly assigned U.S. non-provisional patent application Ser. No. 12/414,709, entitled Implantable Devices for Treatment of Urinary Incontinence, filed on Mar. 31, 2009, which is hereby incorporated by reference in its entirety to this specification.

In one embodiment, body 150 defines a through-channel 154 and a plurality of flanges 156 protruding from a distal end 158 of body 150 and separated by webs 160. In one embodiment, collar 152 defines apertures 162a,b that permit frictional sliding engagement and passage of connection line 120 between body 150 and collar 152. In one embodiment, connection line 120 is disposed through a first aperture 162a of collar 152, around a partial circumference of body 150, and through a second aperture 162b of collar 152. Thus, line 120 contacts both body 150 and collar 152. Body 150 and collar 152 exert a compressive force on connection line 120, which causes frictional interference between connection line 120, body 150, and collar 152. Adjustable anchor 140 is configured to slide bi-directionally along connection line 120 when a sufficient force is applied to adjustable anchor 140 to overcome the frictional interference of its contacting components.

It is to be understood that an amount of compressive force and thus the desired frictional interference between connection line 120, body 150, and collar 152 can be selectively varied through an appropriate selection of material composition and geometry. For example, the compressive force and the frictional interference between connection line 120, body 150, and collar 152 can be selectively varied by fitting collar 152 more tightly against line 120 and body 150. Alternatively, if apertures 162a,b are spaced farther apart in one embodiment of anchor 140 than in a second embodiment of anchor 140, then the compressive force and resulting frictional interference of the first embodiment would be greater than that of the second embodiment due to, comparatively, a longer contact path between connection line 120 and body 150/collar 152.

In one embodiment, both anchors 140, 142 are provided as adjustable anchors that are configured to slide along the respective one of the connection lines 120, 130 to enable selective positioning of support 104 and bladder 106 anatomically within a patient.

With additional reference to FIG. 4, pump 102 includes resilient bulb 110 that is sized to contain a volume V of liquid. Squeezing bulb 110 ejects the liquid through the valve housing 112, across ball valve 80 (FIG. 2), and through conduit 108 into inflatable bladder 106. In one embodiment, it is desirable to provide the surgeon with flexibility in customizing the length of conduit 108 to accommodate various sizes of patients. To this end, in one embodiment pump conduit 114 is provided with a length that is configured to be cut to size, and inflatable bladder 106 is provided with a bladder conduit 170 having a length that is configured to be cut to size. After the surgeon cuts the length of pump conduit 114 and bladder conduit 170 to size, the two sections are joined in a durable and leak-resistant manner with a connector 172.

Figure 6A:
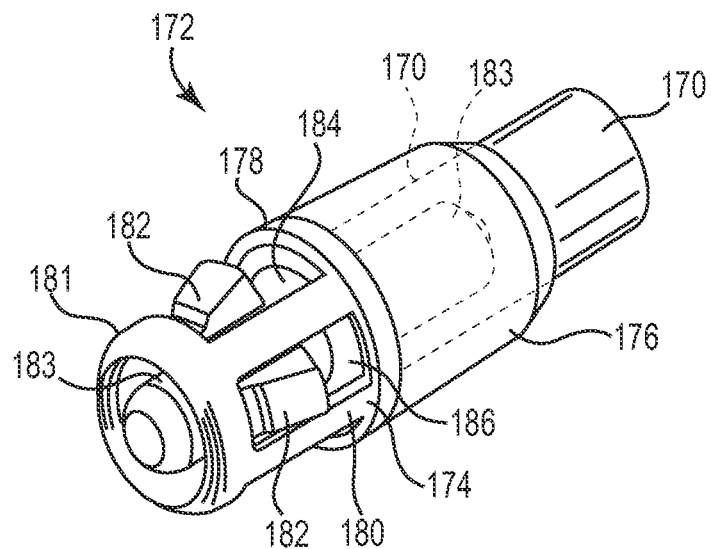
FIG. 6A is a perspective view and FIG. 6B is a cross-sectional view of a connector employed to couple a pump conduit to an inflatable bladder conduit according to one embodiment.
Figure 6B:
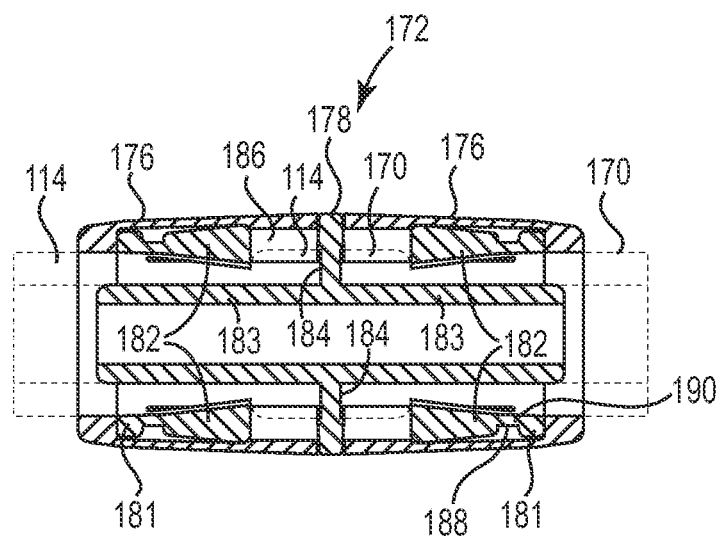

FIG. 6A is a perspective view and FIG. 6B is a cross-sectional view of connector 172 employed to couple pump conduit 114 to bladder conduit 170.

In one embodiment, connector 172 includes a body 174 and collets 176 (one of which is shown in FIG. 6A). Body 174 includes a radial flange 178, a tubular cage 180 on each side of radial flange 178 that terminates in an end ring 181, where each tubular cage 180 is provided with one or more chucks 182. Each of the collets 176 is configured to slide over a section of conduit 114, 170 and onto the tubular cage 180, which will displace the chucks 182 radially inward to exert radial compression onto conduits 114, 170.

In one embodiment, a mandrel 183 extends from each opposing face of radial flange 178, and flange 178 includes an undercut surface 184 configured to provide a stop for the ends of the inserted conduits 114, 170. Mandrels 183 are sized to fit inside an inside diameter of each conduit 114, 170 to establish a flow path through connector 172. End rings 181 are sized to surround an outside diameter of conduits 114, 170.

In one embodiment, tubular cage 180 defines clearance apertures 186 adjacent to radial flange 178. In one embodiment, end rings 181 include grooves 188 that provide webs 190 of reduced thickness between end rings 181 and chuck 182, thereby forming a flexible hinge that enables inward deflection of chucks 182 as collets 176 are advanced over tubular cages 180. For example, after the surgeon cuts conduits 114, 170 to a desired length, one of the collets 176 is placed over each of the conduits 114, 170 and mandrels 183 are inserted into conduits 114, 170. The ends of conduits 114, 170 are seated against radial flange 178, and the collets 176 are slid over tubular cages 180 and conduits 114, 170. The collets 176 deflects chucks 182 inward to exert a radial pinching force around a periphery of conduits 114, 170, which forms a durable connection between the two spliced conduits 114, 170.

Augmentation devices 20, 100 are implantable into a human body of a patient to enable the patient to controllably impede liquid flow through their urethra or other duct. The compact size and limited number of components of the augmentation devices 20, 100 enable the surgeon to implant the devices in a short time frame that has the potential to limit the time, expense, and known side-effects and risks associated with other longer surgical urinary incontinence procedures.

Figure 7:
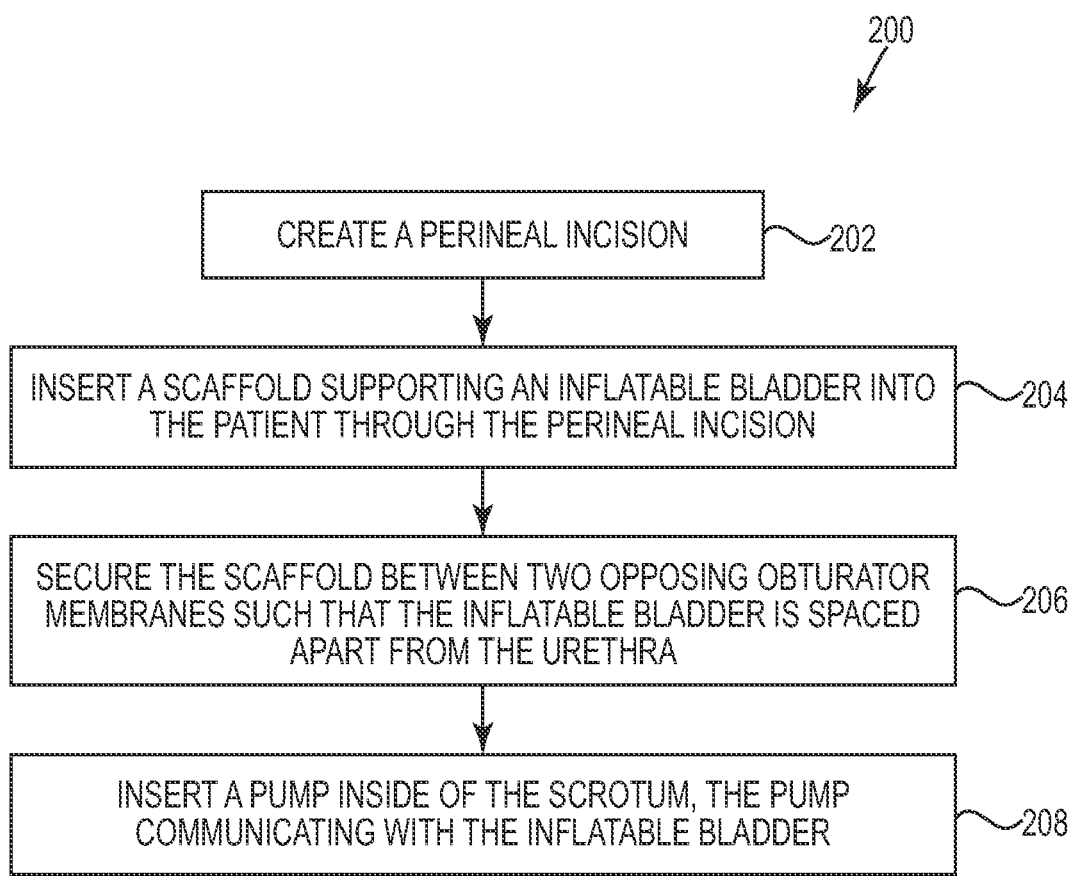
FIG. 7 is a flow diagram of a method of surgically implanting a urethra augmentation device into a patient according to one embodiment.

FIG. 7 is a flow diagram 200 of a method of surgically implanting one of the augmentation devices 20, 100 into a patient according to one embodiment. The method includes creating a perineal incision at 202. In one embodiment, a single perineal incision is created allowing direct access for the surgeon to place the augmentation devices 20, 100 near the patient's urethra. At 204, the method includes inserting a support supporting an inflatable bladder into the patient through the perineal incision. At 206, the method includes securing the support between two opposing obturator membranes such that the inflatable bladder is spaced apart from the urethra. In one embodiment, the inflatable bladder is spaced apart from the bulbous spongiosum that surrounds urethra, which avoids having to separate the bulbous spongiosum from the urethra, thus providing shorter surgical time than is conventional with other incontinence-correcting procedures. At 208, the method includes inserting a pump inside of the scrotum, the pump communicating with the inflatable bladder.

Figure 8:
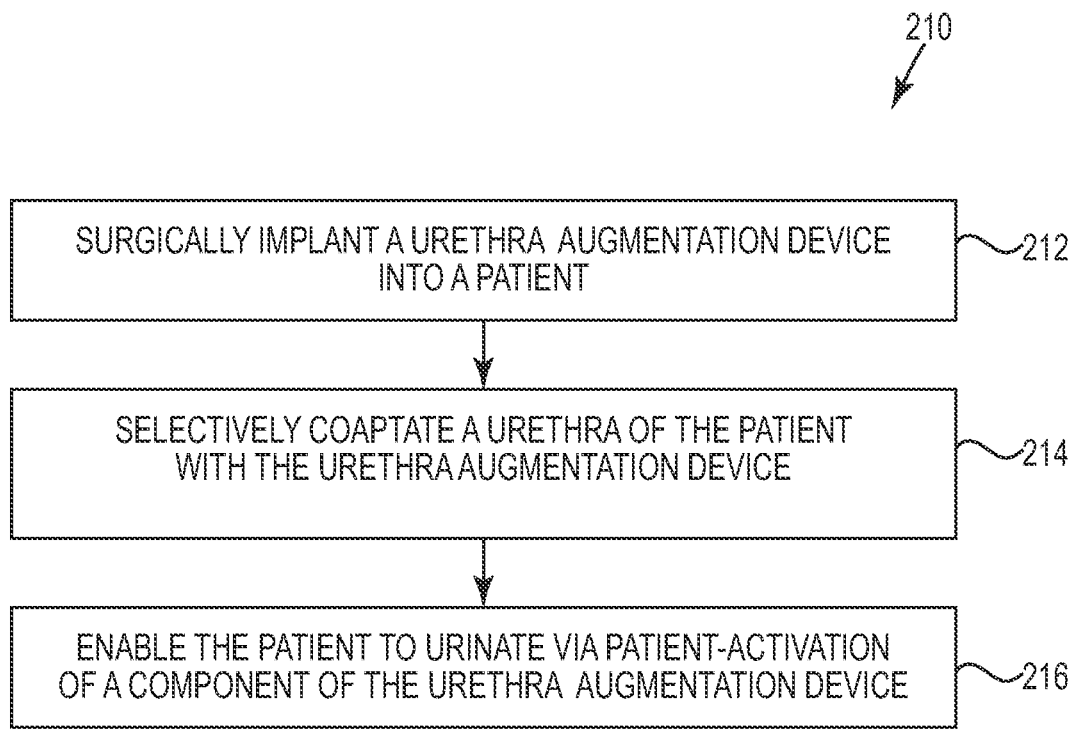
FIG. 8 is a flow diagram of a method of providing a patient with continence control according to one embodiment.

FIG. 8 is a flow diagram 210 of a method of providing a patient with continence control according to one embodiment. The method includes surgically implanting a urethra augmentation device into the patient at 212. For example, and with reference to FIG. 4, one of the augmentation devices 20, 100 is implanted preferably via a single perineal incision as referenced above such that support 104 of the device is near or adjacent to the patient's urethra. At 214, the method includes selectively coaptating a urethra of the patient with the urethra augmentation device. For example, in one embodiment the patient squeezes bulb 110 of pump 102 to inflate inflatable bladder 106 with liquid from bulb 110. Since support 104 of the device is near the patient's urethra, inflating the inflatable bladder 106 results in compression of the urethra. At 216, the method includes enabling the patient to urinate via patient-activation of a component of the urethra augmentation device. For example, in one embodiment the patient activates the pressure relief feature 116 to permit the liquid within inflatable bladder 106 to return to bulb 110, thus deflating the inflatable bladder 106. Deflation of inflatable bladder 106 allows the patient's urethra to open for the passage of urine.

Figure 9A:
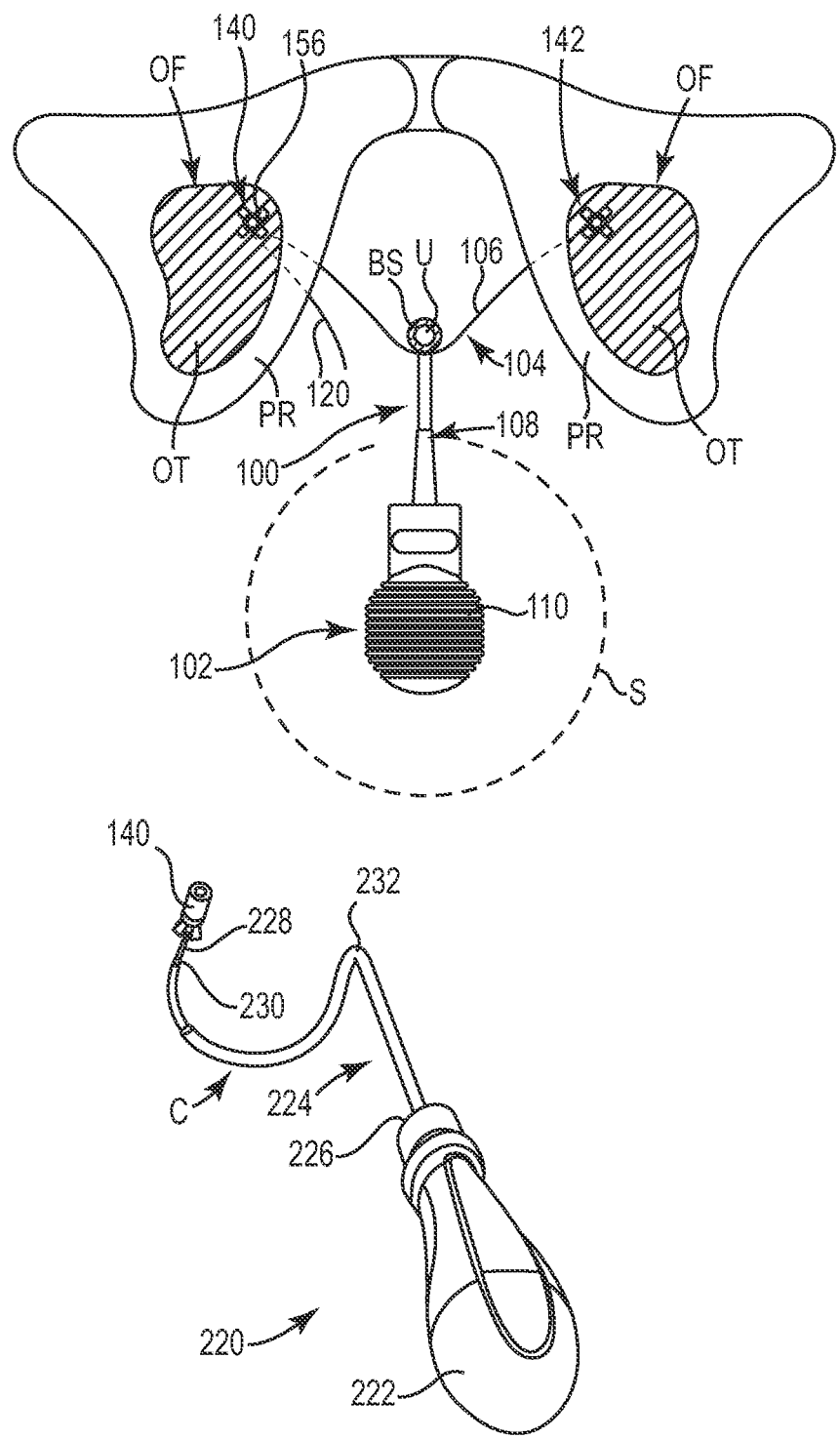
FIGS. 9A and 9B are schematic diagrams of the anatomical augmentation device illustrated in FIG. 4 implanted in a male patient with the sub-urethral inflatable bladder deflated according to one embodiment.

FIG. 9A is a schematic diagram of anatomical augmentation device 100 anchored to obturator tissue OT of a male patient with inflatable bladder 106 deflated and positioned relative to the patient's urethra U according to one embodiment.

In one embodiment, support 104 of device 100 is implanted in a pelvic region PR through a single perineal incision, and pump 102 is implanted in the patient's scrotum S by blunt dissection of the scrotum S. Fixed anchor 142 is secured to obturator tissue OT of one obturator foramen OF and adjustable anchor 140 is secured to obturator tissue OT in the other obturator foramen OF. In one embodiment, both anchors 140, 142 are configured as adjustable anchors. Flanges 156 secure anchors 140, 142 to the obturator tissue OT to maintain device 100 in position relative to urethra U. Implantation of device 100 results in support 104 positioned under the bulbous spongiosum BS surrounding the patient's urethra U. Advantageously, in one embodiment the bulbous spongiosum BS is not dissected off of the urethra, and inflatable bladder 106 configured to enable patient-control of device 100 to selectively coaptate the urethra U through the surrounding bulbous spongiosum BS. If desired, positions of anchors 140, 142 could be exchanged in a left and right sense relative to pelvic region PR.

In one embodiment, a tool 220 is employed to implant device 100 in a patient. Typically, a pair of such tools 220 is employed, including a left hand tool and a right hand tool 220 (illustrated), with such designations referring to a patient's left and right sides, respectively. Generally, the tools are identical except for a direction of each tool's helical curve C.

Tool 220 includes a handle 222 coupled to a shaft 224 having a proximal end 226 and a cylindrical distal tip 228. Handle 222 may have any desired shape or configuration with respect to ergonomic and other considerations of interest. A generally helical curve C is provided in shaft 224. Helical curve C terminates in a shoulder 230 proximate to distal tip 228. In use as described below, helical curve C is advantageously configured to guide tip 228 from an incision (e.g., a vaginal incision in a female patient or a perineal incision in a male patient), around a descending pubic ramus PR, and through obturator foramen OF in the patient. In this example, cylindrical distal tip 228 is configured to be placed through cylindrical channels 154 of adjustable anchor 140 and fixed anchor 142. When so placed, shoulder 230 abuts the body of anchor 140 adjacent to flanges 156 and anchor 140 is thereby carried on tip 228 of tool 220.

In one embodiment, handle 222 has a length of 11.43 cm (4.5 in.); a length of shaft 610, from handle 620 to a beginning point 232 of curve C is 17.78 cm (7.0 in.); shaft 224 has a diameter of 3 mm (0.12 in.) decreasing to 1 mm (0.04 in.) at shoulder portion 230; and curve C has a radius of curvature in a range of 2.03 cm (0.80 in.) to 2.54 cm (1.0 in.). Suitable materials for construction of handle 222 include, for example, thermoplastic or thermoset material, preferably having both high and low durometer regions for ergonomic considerations. A suitable material for construction of shaft 610 is, for example, stainless steel. Tool 200 is disposable, or alternatively, sterilizable and reusable.

In one embodiment, a length of distal tip 228 is chosen so that it protrudes from anchor 140 seated on shoulder 230. When constructed from stainless steel as aforementioned, relatively stiff tip 228 is thereby configured to pierce tissue.

One example of a surgical method to implant device 100 for treatment of urinary incontinence in a patient follows. Although the following procedure is described in relation to male anatomy in which the device is employed to support the male urethra, one of ordinary skill in the art will realize that similar such procedures relating to implanting embodiments of the device into female anatomy are also possible. For example, in one embodiment device 100 is implanted in a female patient to support the female urethra with substantially zero tension applied to the urethra. In one embodiment, device 100 is implanted in a female patient to support the female urethra with a non-zero tension applied to the urethra.

A catheter is placed in the patient's urethra U, among other usual and preliminary steps in preparation for surgery. The patient is placed on an operating table in a slightly exaggerated lithotomy position with buttocks extending just beyond an edge of the table. With the patient under anesthesia, a vaginal incision (female) or a perineal incision (male) is made followed by blunt dissection. In one embodiment of the method, fixed anchor 142 is first placed in obturator tissue OT on the patient's left side, followed by placement of support 104, with subsequent placement of adjustable anchor 142 in obturator tissue OT on the patient's right side.

Accordingly in this embodiment, fixed anchor 142 is placed on distal tip 228 of a left hand tool having an orientation of helical curve C configured to correspond to the patient's left side. Tip 228 of left hand tool, with fixed anchor 142 seated thereupon, is placed within the incision. Left hand tool is then rotated such that rotation of helical curve C advances tip 228 and fixed anchor 142 in a path around a descending pubic ramus PR on the patient's left side, continuing in that path until fixed anchor 142 penetrates obturator tissue OT on the patient's left side (as may be indicated by an audible or tactile "pop") to indicate fixed anchor 142 has thus been secured in obturator tissue OT. Fixed anchor 142 is inhibited from being pulled back through obturator tissue OT by virtue of flanges 156. Left hand tool is then removed from the patient.

Next in this embodiment, adjustable anchor 140 is placed on distal tip 228 of right hand tool 200 having an orientation of helical curve C corresponding to the patient's right side. Tip 228 of right hand tool 200, with adjustable anchor 140 seated thereupon, is placed within the incision. Right hand tool 200 is then rotated such that rotation of helical curve C advances tip 228 and adjustable anchor 140 in a path around a descending pubic ramus (PR) on the patient's right side, continuing in that path until adjustable anchor 140 penetrates obturator tissue OT on the patient's right side (as indicated by an audible or tactile "pop") to indicate adjustable anchor 140 has thus been secured in obturator tissue OT. Adjustable anchor 140 is inhibited from being pulled back through obturator tissue OT by virtue of flanges 156. Right hand tool 600R is then removed from the patient.

Device 100 is preferably placed with inflatable bladder 106 deflated. With device 100 thus placed and secured in the patient by way of fixed anchor 142 and adjustable anchor 140, an assessment is made of whether support 104 is unacceptably loose or tight under urethra U. If support 104 is unacceptably loose, then an end of connection line 120 is pulled away from adjustable anchor 140 with a force sufficient to overcome the aforementioned interference force between connection line 120 and adjustable anchor 140. Connection line 120 thus passes through anchor 140 with a resultant shortening of a distance between support 104 and adjustable anchor 140. Thereby support 104 is raised or elevated under urethra U as desired.

Conversely, if support 104 is unacceptably tight, then connection line 120 and support 104 are pulled away from adjustable anchor 140 with a force sufficient to overcome the interference force between connection line 120 and adjustable anchor 140. Line 120 thus passes through anchor 140 with a resultant lengthening of a distance between support 104 and adjustable anchor 140. Thereby support 104 is lowered under urethra U as desired.

The above-recited process of shortening and lengthening a distance between support 104 and adjustable anchor 140 may be repeated in any order and as frequently as necessary to provide optimal sub-urethral support from support 104 to urethra U. The incision is subsequently closed and usual post-operative procedures are performed. After a suitable surgeon-determined time for healing, a volume of liquid is post-surgically injected into bulb 110 and inflatable bladder 106 is inflated sufficiently to occlude urethra U. The surgeon may choose to adjust the volume of liquid in bulb 110 at this stage to control the rate and pressure of the inflation of inflatable bladder 106.

Device 100 enables the surgeon to selectively adjust the location of support 104 relative to urethra U. The distance between the obturator foramen OF and the urethra will vary by individual, and device 100 desirably provides the surgeon with adjustability to accommodate the different sizes of these individuals.

Figure 9B:
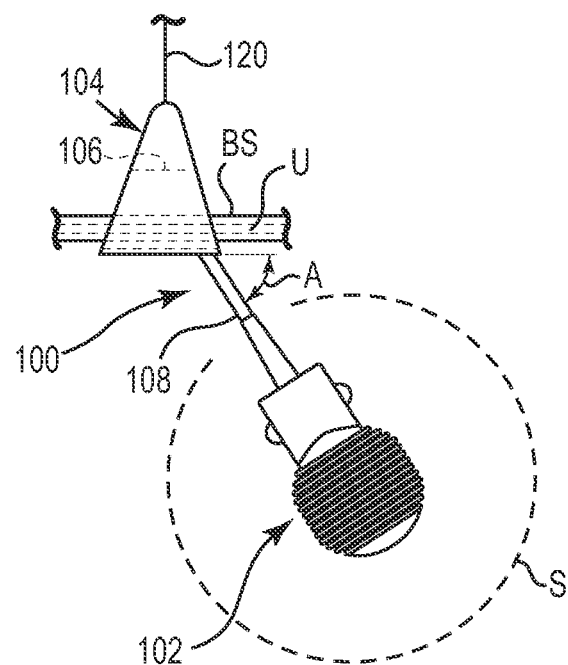

FIG. 9B is a schematic side view of the implanted anatomical augmentation device 100 illustrating pump 102 located inside scrotum S. Support 104 provides support to urethra U, the portion of which that it is desirable to support being generally located distal of scrotum S. In one embodiment, conduit 108 extends from support 104 and inflatable bladder 106 at an angle A relative to a base of support 104 to comfortably and efficaciously locate pump 102 in scrotum S (proximal to support 104) without binding urethra U. In one embodiment, the angle A ranges from approximately zero degrees to approximately 90 degrees. In one embodiment, conduit 108 is flexible to enable the surgeon to selectively adjust the angle A between approximately 0-90 degrees.

Figure 9C:
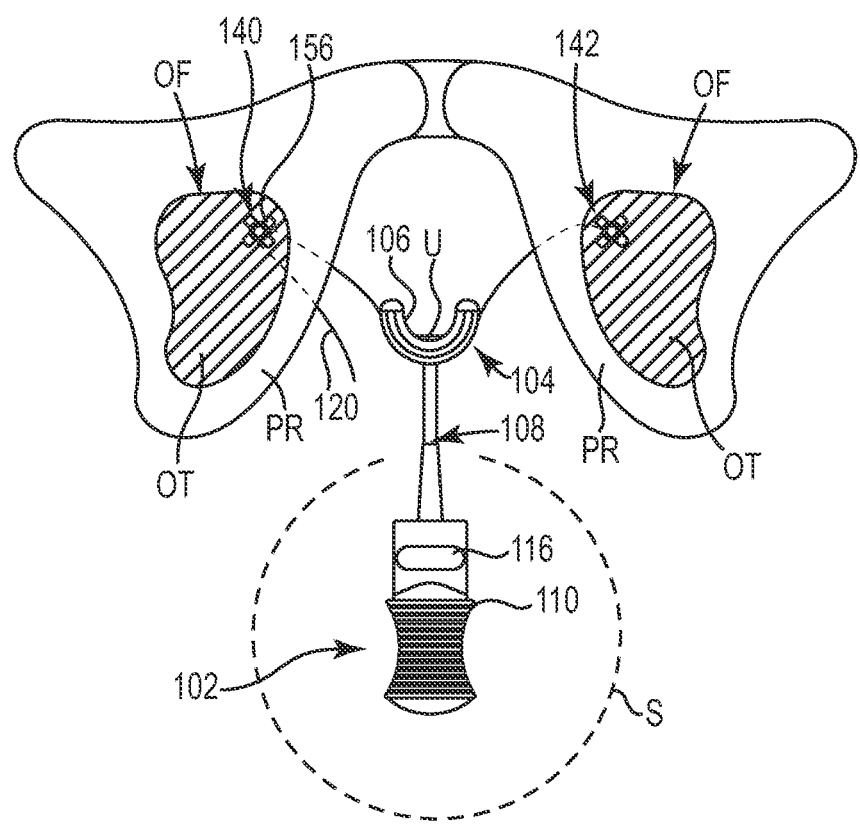
FIG. 9C is a schematic diagram of the anatomical augmentation device illustrated in FIG. 9A with the inflatable bladder inflated to selectively coaptate the patient's urethra according to one embodiment.

FIG. 9C is a schematic diagram of anatomical augmentation device 100 with inflatable bladder 106 inflated to coaptate the patient's urethra U according to one embodiment. After implantation of device 100, anchors 140, 142 secure support 104 in the desired surgeon-located position relative to the urethra U. In one embodiment, support 104 is formed of an open mesh that is configured to enable tissue in-growth over a short period of patient healing time, which further contributes to desirably fixing device in the surgeon-located position.

After an appropriate length of physician-determined healing time, the patient controls the amount of inflation of inflatable bladder 106. For example, as illustrated in FIG. 9C, bulb 110 has been compressed, the compression of which injects liquid from bulb 110 into inflatable bladder 106, thus inflating bladder 106 and compressing urethra U. In one embodiment, the resiliency of bulb 110 and the liquid volume of, for example, sterile saline within bulb 106 is configured to enable the patient to inflate inflatable bladder 106 with one squeeze of bulb 110 to a level that is sufficient to coaptate urethra U. In this manner, the patient controls the closing of urethra U and thus controls continence.

The patient is also in control of opening the urethra U, either for nighttime comfort when the urge to void is reduced or for passing urine. For example, when the patient presses on pressure relief feature 116, ball valve 80 is displaced from seat 84 (FIG. 2) to provide a pathway for the liquid inside inflatable bladder 106 to flow down into bulb 110, thus deflating inflatable bladder 106 and opening urethra U. Selectively deflating bladder 106 during the nighttime when the urge to void is reduced has the added benefit of reducing compression of the urethra when such compression isn't desired by the patient or anatomically called for. Thus, erosion of the urethra is reduced or eliminated.

In one embodiment, bulb 110 is suited for receiving additional liquid volume post-surgically, for example by a physician who delivers additional liquid to bulb 110 through the scrotum S via a needle/syringe. To this end, one embodiment of bulb 110 includes a self-sealing port that is punctured to receive additional liquid delivered through the scrotum S via a needle/syringe, where the self-sealing port seals the puncture opening when the syringe is removed.

FIGS. 10A-11B illustrated various embodiments of inflatable supports for other embodiments of augmentation devices, the supports configured for connection with pump 22 illustrated in FIG. 2 and suited for coaptating a tubular flow member in a human body.

FIG. 10A is a perspective view of one embodiment of an implantable device 250 including an inflatable member 252 in a deflated state and FIG. 10B is a perspective view of implantable device 250 illustrating inflatable member 252 in an inflated state. Device 250 provides a rectilinear flat pillow form and includes an inflatable member 252 and a conduit 254 in fluid communication with inflatable member 252. In one embodiment, device 250 is integrally molded to provide a linear (i.e., flat) inflatable member 252 that is suitably supported with connection lines similar to lines 30, 40 (FIG. 1). In one embodiment, device 250 includes a linear inflatable member that is supported by a polymer mesh in a manner similar to how bladder 106 (FIG. 4) is supported by mesh support 104 (FIG. 4). In any regard, device 250 need not be curved in order to provide compression to tubular members when inflatable member 252 is inflated with a volume V of liquid. In one embodiment, linear inflatable member 252 inflates symmetrically to provide compression to tubular members (e.g., a urethra) when inflated with a volume V of liquid. In the illustrated embodiment, conduit 254 is attached off-center relative to inflatable member 252 and descends at the angle A for connection with pump 22 (FIG. 2).

Figure 11A:
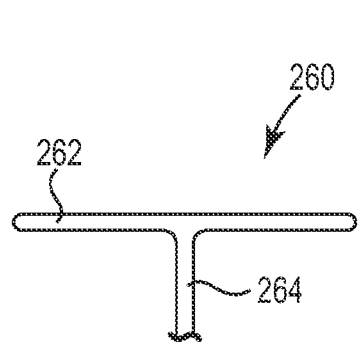
FIG. 11A is a side view of one embodiment of a deflated bladder and FIG. 11B is a side view of the bladder in an inflated state.
Figure 11B:
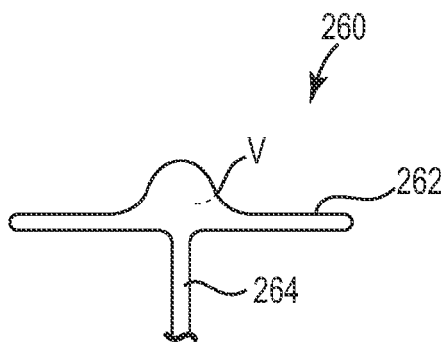

FIG. 11A is a perspective view of one embodiment of an implantable device 260 including an inflatable member 262 in a deflated state and FIG. 10B is a perspective view of implantable device 260 illustrating inflatable member 262 in an inflated state. Device 260 includes an inflatable member 262 and a conduit 264 in fluid communication with inflatable member 262. In one embodiment, inflatable member 262 includes a region R having increased elasticity as compared to the remaining portion of inflatable member 262. When inflatable member 262 is inflated, region R expands more than the remaining portion of inflatable member 262. In one embodiment, region R is located centrally relative to inflatable member 262, although off-center or non-symmetric locations for region R relative to inflatable member 262 are also acceptable.

In one embodiment, device 260 is integrally molded to provide a linear (i.e., flat) inflatable member 262 that is suitably supported with connection lines similar to lines 30, 40 (FIG. 1). In one embodiment, device 260 includes a linear inflatable member that is supported by a polymer mesh in a manner similar to how bladder 106 (FIG. 4) is supported by mesh support 104 (FIG. 4). When selectively inflated by the patient, inflatable member 262 inflates and region R expands disproportionally greater than the remaining portion of inflatable member 262 to provide compression to tubular members when inflated with a volume V of liquid.

Figure 12A:
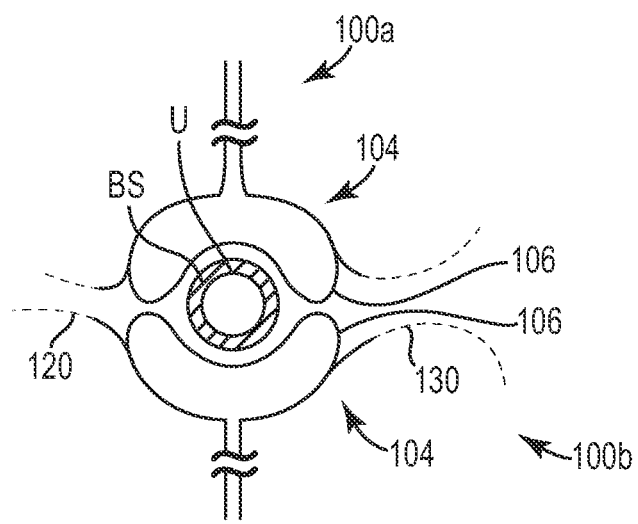
FIGS. 12A and 12B are schematic diagrams of a pair of the anatomical augmentation devices as illustrated in FIG. 4 employed as an artificial sphincter disposed around a urethra according to one embodiment.
Figure 12B:
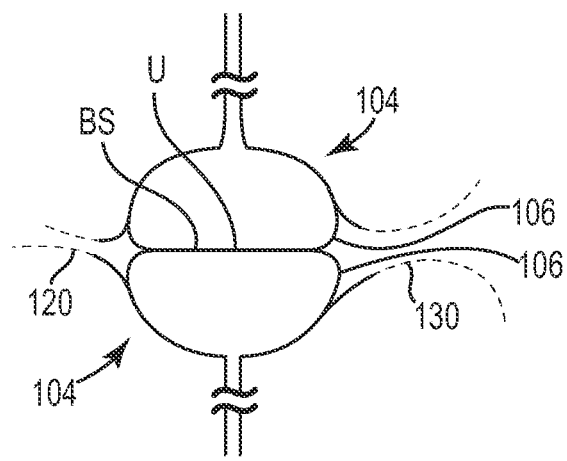

FIGS. 12A and 12B are schematic diagrams of a portion of a pair of anatomical augmentation devices 100a, 100b as illustrated in FIG. 4 employed as an artificial sphincter disposed around a urethra according to one embodiment. Some patients may experience damage to their urethra arising from accident or disease, which can result in an inability to close the urethra. Severe cases of the inability to close the urethra result in a "straight-pipe" condition where the urine flows freely from a non-closable the urethra. The "straight-pipe" urethra condition can be repaired by reconstructive surgery, which can be expensive and painful and perhaps provide only short-term or temporary relief.

Embodiments described herein provide a pair of anatomical augmentation devices 100a, 100b that can be implanted with a single perineal incision and blunt dissection of the scrotum to provide an artificial sphincter disposed around an otherwise non-closable urethra.

Each anatomical augmentation device 100a, 100b includes support 104 supporting inflatable bladder 106 where connection lines 120, 130 are suitably attached to patient tissue at a location determined by the surgeon. After implantation, inflatable bladder 106 of device 100a is above the urethra (supra-urethral) and inflatable bladder 106 of device 100b is below the urethra (sub-urethral). In one embodiment, the inflatable bladders 106 are spaced apart from the bulbous spongiosum surrounding the urethra. Each bulb 110 of pump 102 (FIG. 4) is located in the scrotum, or other suitable location as determined by the surgeon.

FIG. 12B illustrates inflation of each inflatable bladder 106 to bi-laterally close urethra U. In use, the patient squeezes each bulb 110 (FIG. 4) to inflate inflatable bladder 106 as described above. The two opposed inflatable bladders 106 expand and combine to compress opposing sides of the bulbous spongiosum and the urethra, thereby offering the patient a patient-controlled sphincter disposed around urethra. Undesirable erosion of the urethra due to wear-induced contact with a foreign object is reduced or eliminated since each inflatable bladder 106 is configured to be placed or offset away from the urethra.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An incontinence treatment device comprising:
   a support including an inflatable bladder, the support is body-implantable to support tissue of a urethra;
   a pump that is body-implantable and configured to be coupled with the inflatable bladder, where the pump is configured to selectively inflate the inflatable bladder to compress the tissue of the urethra;
   a first connection line attached to the support and a second connection line attached to the support;

a first anchor is fixed to the first connection line and a second anchor is coupled to the second connection line, where the second anchor is an adjustable anchor having a body and a collar positioned around a circumference of the body, the collar including a first aperture spaced a distance from a second aperture with the second connection line captured in a sliding relationship between the collar and a portion of the circumference of the body to configure the adjustable anchor to be movable and position-adjustable relative to the second connection line.

2. The incontinence treatment device of claim 1, wherein the support and the inflatable bladder comprise a single integrally formed unit.

3. The incontinence treatment device of claim 1, wherein the support comprises a mesh sling with the first connection line coupled to a first end of the mesh sling and the second connection line coupled to a second end of the mesh sling.

4. The incontinence treatment device of claim 1, wherein the support comprises a mesh provided with openings that are configured to enable tissue-ingrowth through the mesh.

5. The incontinence treatment device of claim 1, wherein the first anchor and the second anchor are each insertable in obturator tissue to position the support including the inflatable bladder relative to bulbous tissue surrounding the urethra.

6. The incontinence treatment device of claim 1, wherein the inflatable bladder has an arcuate curvature.

7. The incontinence treatment device of claim 1, wherein the adjustable anchor is configured to enable positioning of the inflatable bladder at zero tension relative to the urethra.

8. The incontinence treatment device of claim 1, wherein the adjustable anchor is configured to enable positioning of the inflatable bladder at non-zero tension relative to the urethra.

9. The incontinence treatment device of claim 1, wherein the pump comprises:
   a bulb;
   a valve housing coupled to the bulb; and
   a conduit coupled to the valve housing and configured for fluid communication with the inflatable bladder.

10. The incontinence treatment device of claim 9, wherein the bulb comprises a resilient bulb such that a squeeze of the bulb ejects a portion of a volume of fluid through the conduit for inflation of the inflatable bladder.

11. The incontinence treatment device of claim 9, wherein the bulb of the pump is sized for implantation in a scrotum.

12. The incontinence treatment device of claim 9, wherein the valve housing comprises a check valve configured to selectively enable flow of a volume of fluid from the inflatable bladder to the bulb.

13. The incontinence treatment device of claim 9, wherein the inflatable bladder comprises a second conduit coupleable to the conduit of the pump via a lockable interconnector.

14. The incontinence treatment device of claim 13, wherein the second conduit extends from the inflatable bladder at a non-orthogonal angle relative to a base of the inflatable bladder.

15. A body-implantable incontinence treatment device comprising:
   a support including an inflatable bladder;
   a pump that is configured to be coupled with the inflatable bladder, where the pump is configured to selectively inflate the inflatable bladder to compress a urethra in treating urinary incontinence;
   a first connection line attached to the support and a second connection line attached to the support; and
   a first anchor coupled to the first connection line and a second anchor coupled to the second connection line, where each of the first anchor and the second anchor is an adjustable anchor having a body and a collar positioned around a circumference of the body, each collar includes a first aperture spaced a distance from a second aperture, and each of the first connection line and the second connection line is captured in a sliding relationship between the collar and a portion of the circumference of the body to configure each adjustable anchor to be movable and position-adjustable relative to one of the first connection line and the second connection line.

* * * * *